US008222901B2

(12) United States Patent
Chopra et al.

(10) Patent No.: US 8,222,901 B2
(45) Date of Patent: Jul. 17, 2012

(54) SYSTEM AND METHOD FOR INTRACORPOREAL ELASTOGRAPHY

(75) Inventors: Rajiv Chopra, Toronto (CA); Michael John Bronskill, Toronto (CA); Arvin Forghanian-Arani, Barrie (CA)

(73) Assignee: Sunnybrook Health Sciences Centre, Toronto (CA)

( * ) Notice: Subject to any disclaimer, the term of this patent is extended or adjusted under 35 U.S.C. 154(b) by 460 days.

(21) Appl. No.: 12/544,840

(22) Filed: Aug. 20, 2009

(65) Prior Publication Data
US 2010/0045289 A1 Feb. 25, 2010

Related U.S. Application Data

(60) Provisional application No. 61/118,250, filed on Nov. 26, 2008, provisional application No. 61/090,317, filed on Aug. 20, 2008.

(51) Int. Cl.
*G01V 3/00* (2006.01)
(52) U.S. Cl. .................. 324/309; 324/307; 324/306
(58) Field of Classification Search .................. 324/309, 324/307, 306
See application file for complete search history.

(56) References Cited

U.S. PATENT DOCUMENTS

| 5,265,612 | A | 11/1993 | Sarvazyan et al. |
| 5,284,148 | A * | 2/1994 | Dias et al. ........................ 600/463 |
| 5,451,232 | A | 9/1995 | Rhinehart et al. |
| 5,592,085 | A | 1/1997 | Ehman |
| 5,952,828 | A | 9/1999 | Rossman et al. |
| 5,977,770 | A | 11/1999 | Ehman |
| 6,037,774 | A | 3/2000 | Felmlee et al. |
| 6,486,669 | B1 | 11/2002 | Sinkus et al. |
| 6,833,703 | B2 | 12/2004 | Sinkus et al. |
| 6,862,468 | B2 | 3/2005 | Smith |
| 7,034,534 | B2 | 4/2006 | Ehman et al. |
| 7,979,109 | B2 * | 7/2011 | Li ........................... 600/411 |
| 2008/0255444 | A1 | 10/2008 | Li |

OTHER PUBLICATIONS

Dresner et al., "MR Elastography of the Prostate," International Society for Magnetic Resonance in Medicine, 1999.
Dresner et al., "Data Acquisition Improvements in MR Elastography of the Prostate," Proc. International Society for Magnetic Resonance in Medicine, vol. 10, 2002.
Dresner et al., "MR Elastography of Prostate Cancer," Proc. International Society for Magnetic Resonance in Medicine, vol. 11, 2003, p. 578.
Chan et al., "Shear waves induced by moving needle in MR Elastography," Proceedings of the 26th Annual International Conference of the IEEE EMBS, San Francisco, CA, Sep. 1-5, 2004, pp. 1022-1024.

(Continued)

*Primary Examiner* — Louis Arana
(74) *Attorney, Agent, or Firm* — Ziolkowsi Patent Solutions Group, SC (57) ABSTRACT

A system and method for intracorporeal elastography include an intra-luminal vibratory member configured to be positioned within a lumen of an imaging subject and configured to impart mechanical energy into tissue of the lumen. In a preferred embodiment, an external piezoelectric energy source is included and coupled to the vibratory member and configured to cause the vibratory member to longitudinally vibrate, thereby generating shear waves for use with magnetic resonance elastography.

58 Claims, 9 Drawing Sheets

OTHER PUBLICATIONS

Dresner et al., "Temporal Phase Unwrapping Aids 3-D MR Elastography of Prostate Specimens," Proc. International Society for Magnetic Resonance in Medicine, vol. 11, 2004, p. 1765.

Chen et al., "Mechanical Shear Wave Induced by Piezoelectric Ceramics for Magnetic Resonance Elastography," Proceedings of the 2005 IEEE Engineering in Medicine and Biology 27th Annual Conference, Shanghai, China, Sep. 1-4, 2005, pp. 7020-7023.

Chan et al., "Needle Shear Wave Driver for Magnetic Resonance Elastography," Magnetic Resonance in Medicine, vol. 55, 2006, pp. 1175-1179.

Pallwein et al., "Real-time elastography for detecting prostate cancer: preliminary experience," Journal Compilation, 2007 BJU International, vol. 100, pp. 42-46.

Rossman et al., "Piezoelectric Bending Elements for use as Motion Actuators in MR Elastography," Proc. International Society for Magnetic Resonance in Medicine, vol. 11, 2003, p. 1075.

Uffmann et al., "A Piezoelectric Actuator for MR Elastography", Proc. International Society for Magnetic Resonance in Medicine, vol. 10, 2002.

* cited by examiner

SYSTEM AND METHOD FOR INTRACORPOREAL ELASTOGRAPHY

CROSS-REFERENCE TO RELATED APPLICATIONS

This application claims the benefit of U.S. Provisional Application No. 61/118,250, filed Nov. 26, 2008, and U.S. Provisional Application No. 61/090,317, filed Aug. 20, 2008, which are each herein incorporated in their entirety.

FIELD OF THE INVENTION

The present invention relates generally to elasticity imaging for medical diagnosis and treatment evaluation and, more particularly, to the measurement of the stiffness distribution in a region of tissue using an intra-luminal device placed within a body cavity or organ to produce mechanical vibration of adjacent tissue.

BACKGROUND OF THE INVENTION

Many disease processes such as solid tumors and liver fibrosis manifest themselves as changes in tissue mechanical properties. Manual palpation of tissues is an important clinical tool for the detection of disease within the body. Unfortunately, palpation is mostly limited to superficial organs and to the sensitivity of tactile perception.

Elastography is an imaging technique that uses tissue mechanical properties as the source of contrast. Advantages of elastography include the capability to quantify the elastic properties associated with disease and to provide a measure of the spatial distribution of elastic properties within organs to localize regions of altered stiffness. Many elastographic imaging techniques rely on measuring the displacements of tissue via the application of an external force on the tissue. The stiffness distribution is calculated based on the principle that the displacements exhibited by tissues in the presence of a force are determined by the underlying elastic properties. Ultrasound and magnetic resonance imaging (MRI) are both capable of resolving tissue displacements for elastography, and are both being developed in parallel for tissue stiffness imaging. Ultrasound techniques are typically based on tracking the displacement of scatterers along the direction of the ultrasound beam upon manual compression of tissue with a transducer. The technique is limited to measuring static elastic properties and is dependent on the operator.

Magnetic resonance elastography (MRE) is a promising technique that involves application of vibration using a mechanical actuator and measuring the resulting tissue motion using phase-contrast MRI sequences capable of resolving particle displacement in all three dimensions. Dynamic mechanical properties are measured by generating shear waves in the frequency range of 50-1000 Hz. These wave images are used to calculate elastograms, or stiffness maps, in tissue, which can be used as diagnostic tools.

The source of mechanical vibration in MRE is typically applied at the external surface of the body, causing mechanical shear waves to propagate into the body. Unfortunately, shear waves are highly attenuated in the body and are typically limited to less than 10 cm of penetration at frequencies between 50-60 Hz. In addition, the low frequencies used to achieve sufficient penetration result in longer shear wavelengths in tissue that result in lower spatial resolution elastograms.

It is therefore desirable to adapt MRE for the imaging of deep-seated organs at diagnostically viable spatial resolutions. Recently, a system for performing MRE was disclosed by Smith in U.S. Pat. No. 6,862,468, in which an ultrasonic transducer is mounted at the distal end of a catheter. The catheter is inserted into the subject and shear waves are generated locally at the distal end of the catheter by the ultrasonic transducer. MRI images of the resulting shear waves are processed to obtain an elastograph.

While this approach provides an initial step in the development of intracorporeal MRE, it suffers from the disadvantage of requiring that the ultrasonic transducer be mounted and powered at the distal end of the catheter (i.e. the end of the catheter that resides within the subject during imaging). This requirement adds significant complexity to the design of the system and necessitates powering the transducer by electrical leads integrated axially along the catheter. Such an arrangement is costly to produce, may be prone to an increased failure rate, and may also generate unwanted signal artifacts.

What is therefore required is a simple MRE system that does not require the incorporation of an active transduction device at the distal end of a catheter or probe.

SUMMARY OF THE INVENTION

Embodiments of the invention provide a system and method that overcome the aforementioned challenges by providing for the use of an intra-luminal device capable of vibrating adjacent tissue for imaging by a medical imaging device without the need for an active acoustic or ultrasonic transducer to be located within the subject during imaging.

In accordance with one aspect of the invention, an apparatus for intracorporeal elastography includes an intra-luminal vibratory member configured to be positioned within a lumen of an imaging subject and configured to impart mechanical energy into tissue of the lumen. An acoustic energy source is also included and externally coupled to the vibratory member, thereby causing the vibratory member to generate shear waves within the subject.

Accordingly, the present invention provides an apparatus for elastography comprising:

a member, wherein a distal end of said member is adapted to be positioned within a lumen of an imaging subject;

an acoustic energy source provided external to said subject and acoustically coupled to a proximal end of said member;

wherein acoustic energy coupled to said member generates shear waves within said subject.

The invention further provides a method of intracorporeal elastography, said method comprising the steps of:

positioning a distal end of a member within a lumen of an imaging subject;

coupling acoustic energy from an external acoustic energy source to a proximal end of said member, wherein said acoustic energy coupled to said member generates shear waves within said subject; and acquiring medical imaging data of a region of interest of said subject.

In another embodiment, the invention provides a system for elastography comprising:

a member, wherein a distal end of said member is adapted to be positioned within a lumen of an imaging subject;

an acoustic energy source provided external to said subject and acoustically coupled to a proximal end of said member, wherein acoustic energy coupled to said member generates shear waves within said subject; and a medical imaging apparatus configured to detect a response of tissue to said shear waves.

Various other features and advantages of the present invention will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION OF THE INVENTION

Generally speaking, the systems described herein are directed to an intra-luminal vibratory device for magnetic resonance elastography. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to an intra-luminal vibratory device for magnetic resonance elastography.

As used herein, the term "acoustic" refers to audible, sonic and ultrasonic vibrations and/or waves. Vibrations may comprise, but are not limited to, oscillatory mechanical motion of a rigid material, mechanical vibrations and/or waves propagating in an elastic material, and pressure waves propagating within a hydraulic or pneumatic fluid.

As used herein, the term "acoustic energy" refers to energy stored in the form of acoustic vibrations or waves.

As used herein, the term "acoustic energy source" refers to an actuator, transducer or other device capable of generating acoustic vibrations and/or waves. Exemplary acoustic energy sources include, but are not limited to, electro-acoustic devices such as audio speakers, devices adapted to produce oscillatory linear motion such as linear motors, piezoelectric transducers, ultrasonic transducers, magneto-acoustic transducers, pneumatic devices adapted to couple acoustic vibrations into a pneumatic fluid, surface acoustic wave transducers, micro-electro-mechanical systems and electromagnetic acoustic transducers.

As used herein, the coordinating conjunction "and/or" is meant to be a selection between a logical disjunction and a logical conjunction of the adjacent words, phrases, or clauses. Specifically, the phrase "X and/or Y" is meant to be interpreted as "one or both of X and Y" wherein X and Y are any word, phrase, or clause.

As used herein, the terms, "comprises" and "comprising" are to be construed as being inclusive and open ended, and not exclusive. Specifically, when used in this specification including claims, the terms, "comprises" and "comprising" and variations thereof mean the specified features, steps or components are included. These terms are not to be interpreted to exclude the presence of other features, steps or components.

Figure 1:
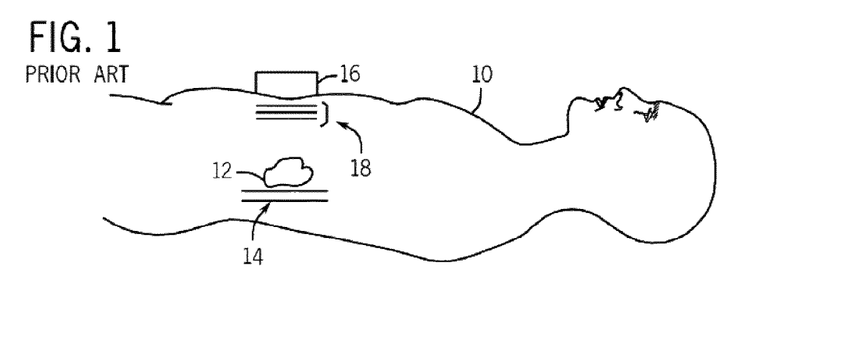
FIG. 1 is an MRE illustration showing prior art high frequency mechanical wave penetration into an imaging subject via a surface motion device.
Figure 2:
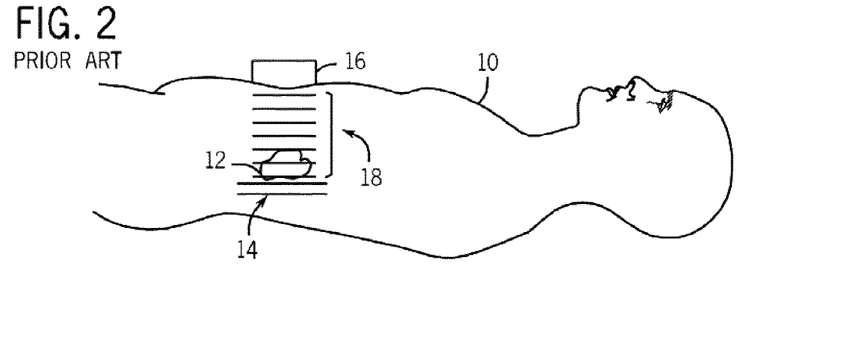
FIG. 2 is an illustration showing prior art low frequency mechanical wave penetration into an imaging subject via a surface motion device.

FIGS. 1 and 2 are magnetic resonance elastography (MRE) illustrations showing prior art high frequency mechanical wave penetration into an imaging subject via a surface motion device. In FIG. 1, a patient 10 is shown with a tissue region of interest 12 close to a body cavity 14. A conventional surface mechanical actuator 16 produces shear waves 18 that travel into the body and are attenuated with distance. If frequencies (such as frequencies greater than 100 Hz) that produce a wave 18 with at least 3-4 wavelengths across the target tissue of interest 12 are used, the waves 18 are attenuated and fail to reach the target location. As shown in FIG. 2, shear waves 18 having a lower frequency may be used such that the tissue region of interest 12 is subject to the shear waves 18. Although shear waves 18 induced by mechanical energy from mechanical actuator 16 are able to propagate to the target tissue region of interest 12, the wavelengths are typically so large that they are not amenable to the detection of small regions of altered stiffness.

Figure 3:
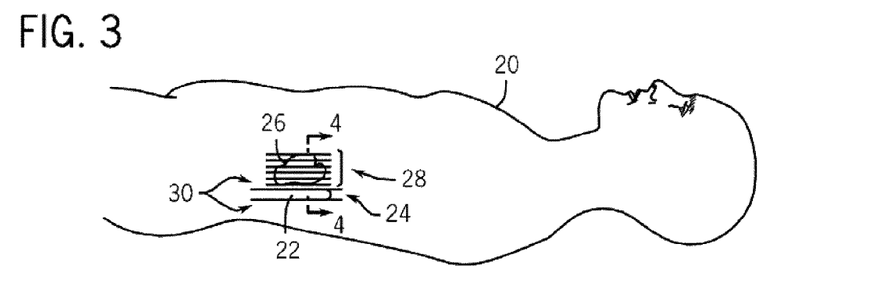
FIG. 3 is an illustration showing mechanical wave penetration into tissue of an imaging subject via a device according to an embodiment of the invention.

FIG. 3 is an illustration showing mechanical wave penetration into tissue of an imaging subject 20 via an intra-luminal member 22 according to an embodiment of the invention. Member 22 is elongated and suitable for insertion into a body cavity or orifice 24 and is placed near a tissue region of interest 26 such that high-frequency mechanical energy may propagate into the tissue region of interest 26. Mechanical energy is imparted to the member 22 to generate oscillatory motion, which results in the generation of mechanical or shear waves 28 that propagate through tissue 30 in the immediate vicinity. The oscillatory motion induces wave motion in the tissue region of interest 26 that can be imaged using MRI methods known in the art. Elongated member 22 can be removed after the measurement or translated along the cavity 24 to interrogate another tissue region of interest.

In a preferred embodiment of the invention, an acoustic energy source external to the imaging subject is acoustically coupled to the proximal end of a member, and the distal end of the member is adapted to be inserted into a lumen of the subject. The acoustic energy coupled to the member causes at least the distal end of the member to mechanically vibrate and generate shear waves within the subject. The member is preferably flexible over at least a portion of its total length to facilitate insertion into, and guidance within, a lumen within the subject.

In a preferred embodiment, the distal end of the member is positioned at a selected location within the subject, and MRE is performed by imaging the shear waves generated by the member with an MRI. Unlike methods known in the prior art, the member is guided within the lumen and passively generates shear waves within the lumen rather than by an active transducer integrated into the distal end of the member.

In one embodiment, the acoustic energy source causes the member to vibrate longitudinally along its axis. In another embodiment, the acoustic energy source causes vibratory motion of the transducer, preferably along its axis. Those skilled in the art will appreciate that mechanical contact between the member and the walls of a lumen or body cavity ensures transfer of mechanical energy to adjacent tissue and the generation of shear waves.

Figure 4:
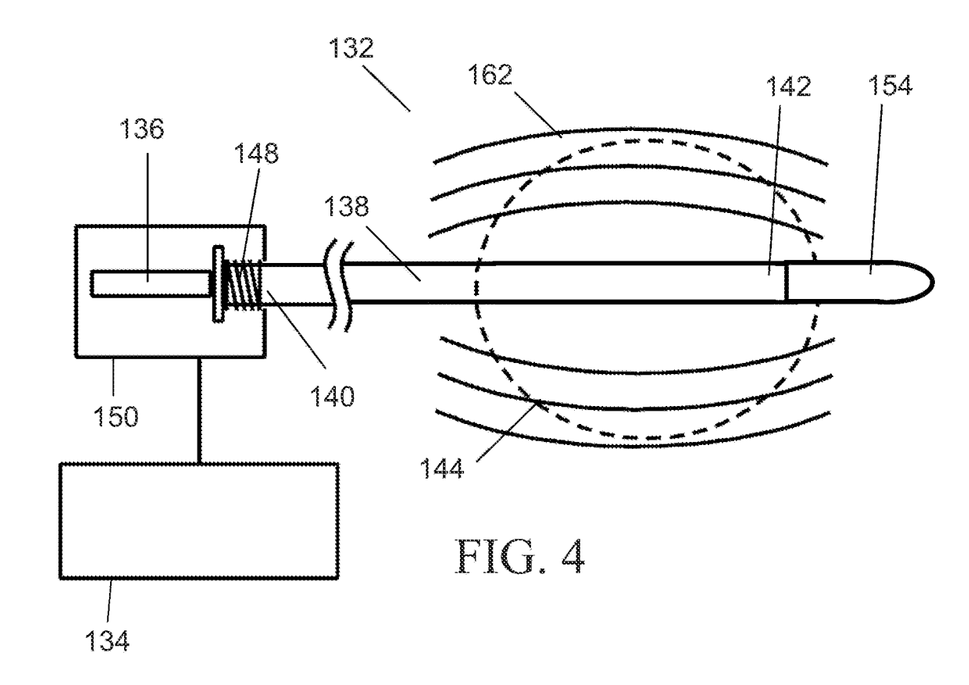
FIG. 4 is an illustration showing an intra-luminal vibratory member positioned in a tissue cavity according to an embodiment of the invention.

FIG. 4 is a schematic diagram showing a preferred embodiment in which an actuator external to the subject is employed to create longitudinal vibrations of a member inserted into a lumen of a subject. System 132 includes a controller 134 coupled to and configured to control an acoustic actuator 136. A member 138 has a first end 140 coupled to acoustic actuator 136 and a second end 142 positioned adjacent to a tissue region of interest 144. In one embodiment, a spring 148 surrounding first end 140 engages both the device 138 and a housing 150 of acoustic actuator 136. The actuator 136 couples acoustic energy into the member, for example, by repeatedly striking a first end 140 of member 138. In this manner, mechanical waves 162 caused by longitudinal vibration of motion member 138 may be projected into tissue 144 as shear waves.

Preferably, acoustic actuator 138 is a piezoelectric actuator. The piezoelectric element is preferably adapted to couple longitudinal vibrations into the vibratory member. For example, the piezoelectric actuator may be attached to a proximal end of the vibratory member, either directly or through an acoustic coupling material. In another embodiment, the piezoelectric actuator may be configured to repeatedly mechanically contact a proximal end of the vibratory member to produce longitudinal vibrations within the member. However, those skilled in the art will appreciate that a wide range of acoustic actuators are contemplated by the invention. For example, the acoustic actuator 138 may be an electromagnetic actuator or a pneumatic actuator.

In a preferred embodiment, member 138 further comprises a flexible tip 154 adapted to assist in the insertion of the member into and through a lumen to a region of interest. In an exemplary embodiment, member 138 includes a rigid brass shaft or tube having, for example, an outer diameter of 6.35 mm, and a flexible tip.

Vibration may be produced via a sinusoidal signal with, for example, a peak voltage of 100V at frequencies within a range of 60 Hz and 3000 Hz. The signal may be low-pass filtered with, for example, a cut-off frequency of 2 kHz, that removes high-frequency noise that might interfere with MR imaging. The signal may be generated in burst or pulsed mode and is preferably controlled such that the MR imaging sequence is synchronized with vibration. A continuous signal may instead be generated if desired.

In some lumen types that are typically narrowed or closed in a subject, insertion of the member into the lumen may provide sufficient contact between the member and the walls of the lumen to support the efficient generation of shear waves in the tissue surrounding the lumen. However, other lumen types may be open or have a larger diameter, which can result in less contact between the member and the lumen.

Figure 5:
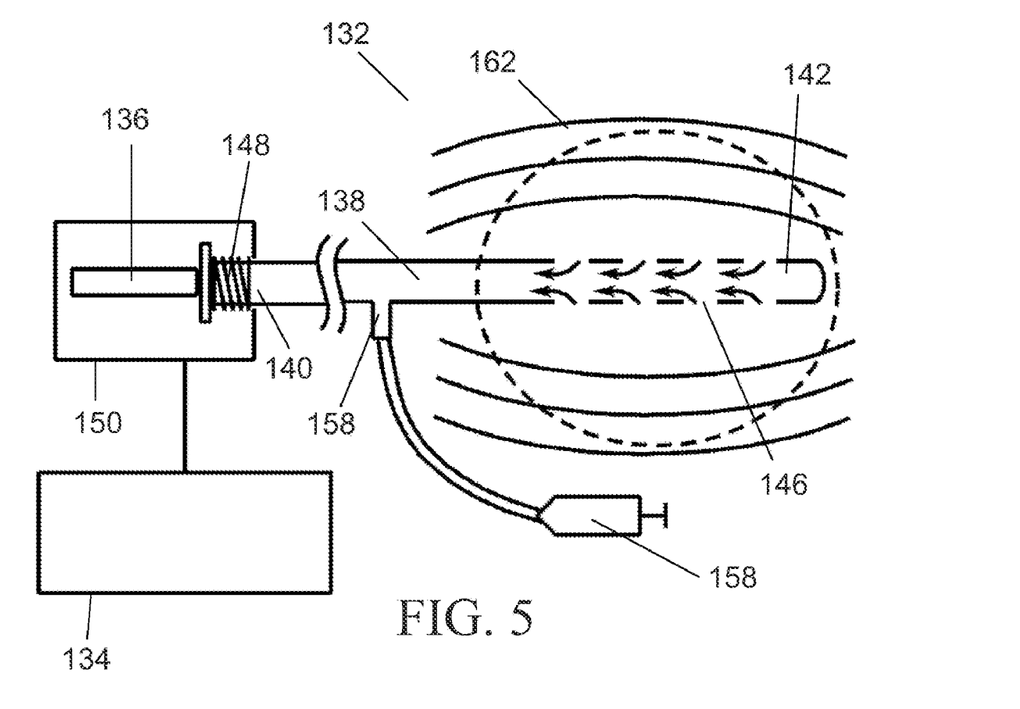
FIG. 5 is an illustration showing an intra-luminal vibratory member adapted to improve the adhesion of the member to the lumen via the inclusion of holes in the member and the application of a negative pressure change.

FIG. 5 shows one embodiment adapted to increase the contact of the member with the lumen, member 138 may include a series of holes or apertures 146 coupled to an inlet port 156 of motion member 138. Inlet port 156 is connectable to a suction device such as a syringe or extractor 158 via a tube 160. In operation, member 138 is moved into position, and extractor 158 creates a pressure differential via holes 146 such that tissue 144 is drawn toward and comes into physical contact with extractor 158. Extractor 158 may be controlled manually or automatically.

In one embodiment, the distal end of member 138 has a shape that is selected to enhance the efficiency of shear wave generation. Distal end may be shaped to locally increase the adhesion of the member to the inner walls of a lumen. The shape may further be configured to efficiently out-couple acoustic waves or direct the generation of shear waves in a selection non-isotropic radiation pattern. Alternatively, the shape may be selected to increase the amount of energy coupled into shear waves relative to the amount of energy coupled into longitudinal waves. In yet another embodiment, the shape is selected to minimize the generation of reflected and/or standing waves inside the member.

Figure 6:
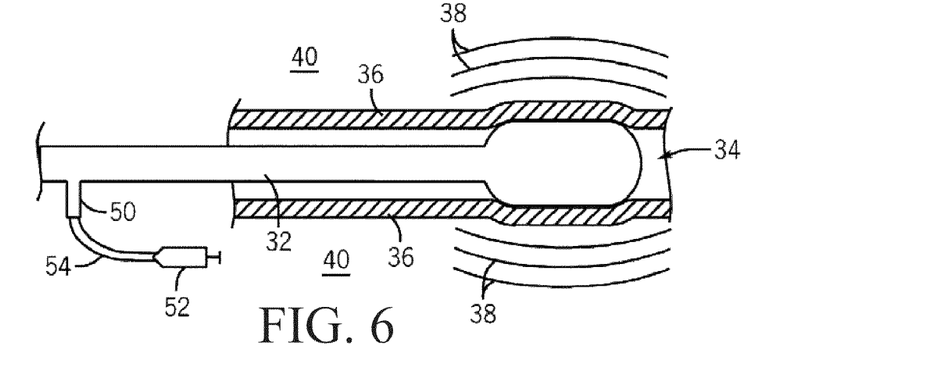
FIG. 6 is an illustration showing an intra-luminal vibratory member positioned in a tissue cavity according to an embodiment of the invention.

FIG. 6 is an illustration showing an embodiment in which member 32 is positioned in a cavity 34 of a lumen or other tubular organ. As shown, member 32 is larger than the natural size of tissue cavity 34, i.e. the member has a diameter that is larger than the diameter of the tissue cavity prior to insertion of the member. Accordingly, walls 36 of tissue cavity 34 spread apart or expand to permit insertion of member 32 into and through tissue cavity 34. In this manner, physical contact and adhesion between walls 36 and member 32 are achieved such that when member 32 is caused to vibrate along its longitudinal axis, shear waves 38 are propagated into tissue 40 surrounding or adjacent to walls 36 of tissue cavity 34.

Figure 7:
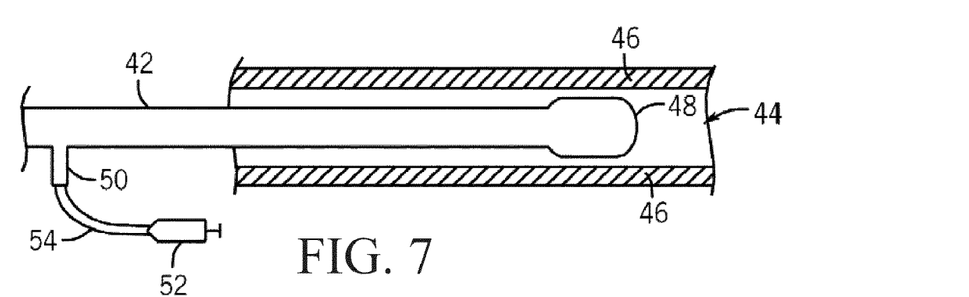
FIG. 7 is an illustration showing an intra-luminal vibratory member having an inflatable portion positioned in a tissue cavity according to an embodiment of the invention.
Figure 8:
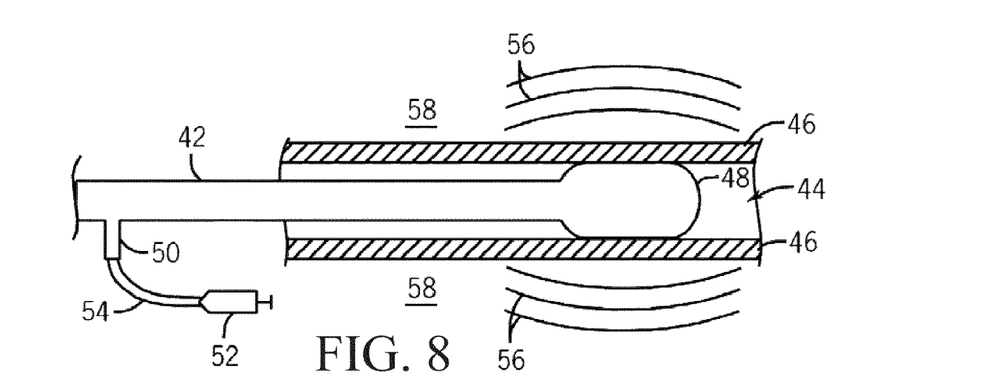
FIG. 8 is an illustration showing the intra-luminal vibratory member shown in FIG. 7 having the inflatable portion inflated in the tissue cavity according to an embodiment of the invention.

FIGS. 7 and 8 illustrate additional embodiments in which member 42 is positioned in a tissue cavity or lumen 44. As shown, member 42 is has a diameter that is smaller than that of a tissue cavity 44. To engage walls 46 of tissue cavity 44, a distal end of member 42 includes an inflatable portion or balloon 48 that may be inflated or enlarged to come into contact with and to adhere to walls 46.

In one embodiment, member 42 includes an inlet port 50 connectable to an inflation device such as a syringe or injector 52 directly or via a tube 54. In operation, member 42 is moved into position, and injector 52 inserts a fluid or gas into balloon 48 such that balloon 48 is inflated to fill a portion of tissue cavity 44 and to come into physical contact with walls 46 as shown in FIG. 8. In this manner, mechanical shear waves 56 caused by vibration of member 42 may be projected into tissue 58 surrounding and adjacent to walls 46 of tissue cavity 44. Injector 52 may be controlled manually or automatically.

Figure 9:
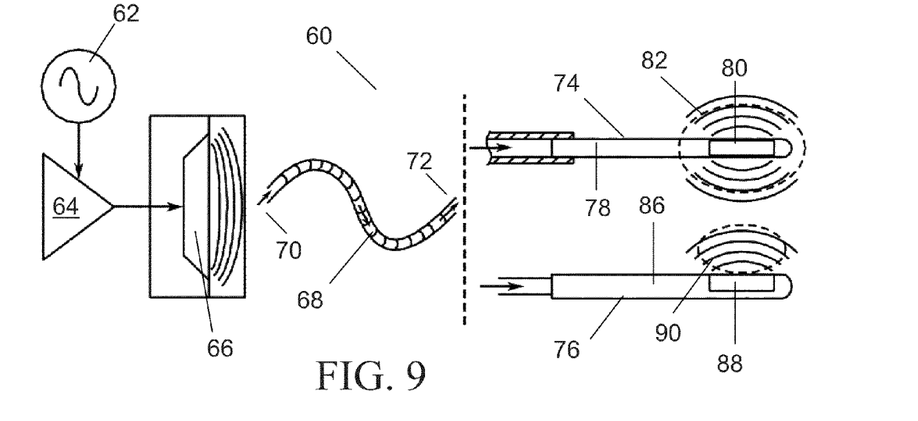
FIG. 9 is a schematic diagram showing a pneumatic intra-luminal vibratory system according to an embodiment of the invention.

In another embodiment of the invention, the member is adapted to include a flexible membrane at its distal end to impart waves into the tissue surrounding the lumen. FIG. 9 is a schematic diagram showing an exemplary pneumatic system 60 according to an embodiment of the invention. System 60 includes a function generator 62 coupled to an audio amplifier 64. Audio amplifier 64 drives an audio output device 66 such as a loudspeaker.

The member comprises a flexible hose 68 and distal member 74, 76. The hose is hermetically coupled to audio output device 66 at a first end 70 and at a second end 72 to distal member 74, 76. A pneumatic fluid (such as air or other gaseous fluid) or a hydraulic fluid is hermetically sealed in hose 68. Hose 68 is preferably non-elastic such that a pressure variance therein may be propagated from first end 70 to second end 72. The distance of hose 68 depends on the MRI-compatibility of audio output device 66. If not MR compatible, audio output device 66 may be placed outside the magnet room.

Distal member 74 may be fluidly and pneumatically coupled to audio output device 66 via hose 68. Distal member 74 includes a hollow body 78 and an elastic or pliable membrane 80, which allows mechanical wave propagation. The vibratory action of membrane 80 produces both longitudinal and shear waves, with shear waves preferentially generated at the edges of the membrane.

Audio output device 66 comprising function generator 62 and audio amplifier 64 induces a time-varying pneumatic pressure at one or more desired frequencies, and acoustic energy is transferred to distal member 74 through hose 68. Application of the time-varying pressure within distal member 74 causes membrane 80 and distal member 74 to vibrate. Through vibration of membrane 80, longitudinal and shear waves 82 are caused to propagate into a tissue region of interest. In one embodiment, distal member 74 is a transurethral device configured to be inserted into and through a urethra or other small lumen.

In another embodiment, also shown in FIG. 9, distal member 76 has a diameter that is larger than that of the hose (or other flexible hollow member containing pneumatic fluid) and is configured to be inserted into and through, for example, a colon or other large lumen. Distal member 76 may be fluidly and pneumatically coupled to audio output device 66 via hose 68. Distal member 76 includes a hollow body 86 and an elastic or pliable membrane 88, which allows directional mechanical wave propagation. Preferably, acoustic energy from audio output device 66 is transferred to distal member 76 through hose 68. Application of the time-varying pressure within distal member 76 causes membrane 88 and distal member 76 to vibrate. Through vibration of membrane 88, longitudinal and shear waves 90 are caused to propagate into a tissue region of interest 92.

In a preferred embodiment, distal member 74, 76 contacts the hose with an opening that allows the fluid to enter the member and directly vibrate the membrane. In an alternative embodiment, distal member may include a second fluid that is in contact with the fluid within the hose via a second membrane located at the interface of the distal end of hose 68 and distal member 74, 76. In yet another embodiment, the member may be a single flexible hollow member within an integrated membrane at its distal end, where the member is directly coupled to the audio output device rather than through an intermediate hose.

Function generator 62 may cause a frequency of the longitudinal and shear waves 82, 90 to be, for example, within a range of 60 Hz and 3000 Hz. Function generator 62 may also be designed to pulse the vibration of distal member 74, 76 synchronously with an imaging sequence of a medical imaging apparatus (not shown) or to continuously vibrate distal member 74, 76.

Figure 10:
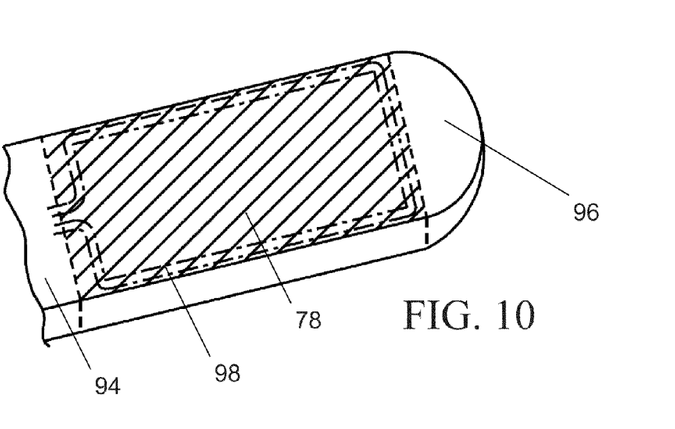
FIG. 10 is a perspective view of one of a distal member according to an embodiment of the invention.

FIG. 10 is a perspective view of a preferred embodiment of distal member 76. Membrane 78 is positioned between a body portion 94 and an end cap 96 of distal member 76. End cap 96 is preferably rounded or tapered so as to ease insertion of distal member 76 into a lumen. Body portion 94 and end cap 96 are preferably rigid while membrane 78 is elastic or pliable and expands outward and inward based on the time-varying pressure within distal member 76.

In one embodiment, a radio-frequency (RF) coil 98 (shown in phantom) suitable for acquiring MRI data may be positioned within distal member 76 for acquiring MRI data local to distal member 76. In one embodiment, coil 98 includes one loop tuned to the resonant frequency of MR signals. Those skilled in the art will appreciate that other coil configurations are possible according to the invention. For example, coil 98 may also include multiple loops or other coil configurations for the transmission and reception of radiofrequency energy, as is known in the art. The use of local RF coils enables the use of small fields of view without the need to compensate for phase wrapping due to the highly localized sensitivity of the coil and provides superior SNR in the immediate tissue due to the proximity of the coil.

Figure 11:
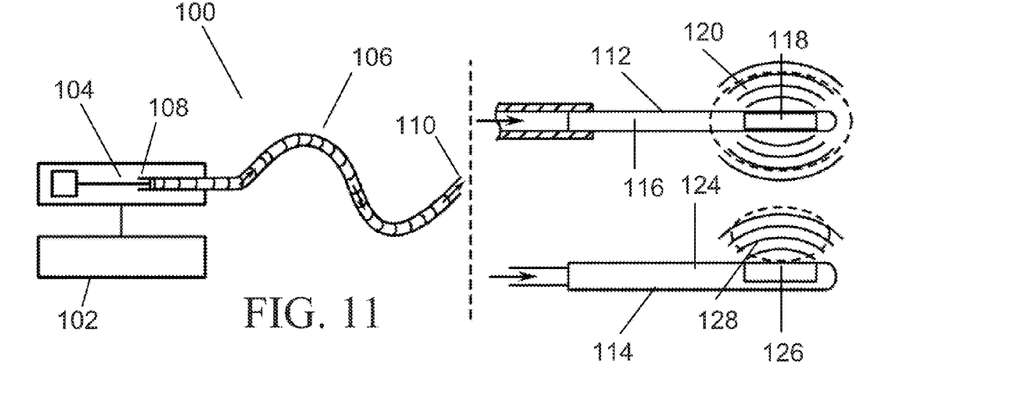
FIG. 11 is a schematic diagram showing a hydraulic intra-luminal vibratory system according to an embodiment of the invention.

FIG. 11 is a schematic diagram showing a hydraulic system 100 according to an embodiment of the invention. System 100 includes a controller 102 coupled to and configured to control a hydraulic actuator 104 such as a piston. A flexible hose 106 is hermetically coupled to hydraulic actuator 104 at a first end 108 and at a second end 110 to a hydraulic distal member 112, 114. Hose 106 is preferably non-elastic such that a pressure variance therein may be propagated from first end 108 to second end 110. A hydraulic fluid such as water or other hydraulic liquid is sealed in hose 106.

In one embodiment, hydraulic distal member 112 is a transurethral device configured to be inserted into and through a urethra or other small lumen. Distal member 112 may be fluidly and hydraulically coupled to hydraulic actuator 104 via hose 106. Distal member 112 includes a hollow body 116 and an elastic or pliable membrane 118, which allows omnidirectional mechanical wave propagation. Via controller 102, hydraulic actuator 104 induces a time-varying hydraulic pressure at one or more desired frequencies, and hydraulic energy is transferred to hydraulic distal member 112 through hose 106. Application of the time-varying hydraulic pressure within distal member 112 causes membrane 118 and distal member 112 to vibrate. Through vibration of membrane 118, longitudinal and shear waves 120 are caused to propagate into a tissue region of interest.

In another embodiment, hydraulic distal member 114 is a device larger than the transurethral device and is configured to be inserted into and through, for example, a colon or other large lumen. Distal member 114 may be fluidly and hydraulically coupled to hydraulic actuator 104 via hose 106. Distal member 114 includes a hollow body 124 and an elastic membrane 126, which allows directional mechanical wave propagation. Hydraulic energy from hydraulic actuator 104 is transferred to hydraulic distal member 114 through hose 106.

Application of the time-varying pressure within distal member 114 causes membrane 126 and distal member 114 to vibrate. Through vibration of membrane 126, longitudinal and shear waves 128 are caused to propagate into a tissue region of interest.

Controller 102 may cause a frequency of the longitudinal and shear waves 120 to be, for example, within a range of 60 Hz and 3000 Hz. Controller 102 may also be designed to pulse the vibration of distal member 112, 114 synchronously with an imaging sequence of a medical imaging apparatus (not shown) or to continuously member 112, 114.

Figure 12:
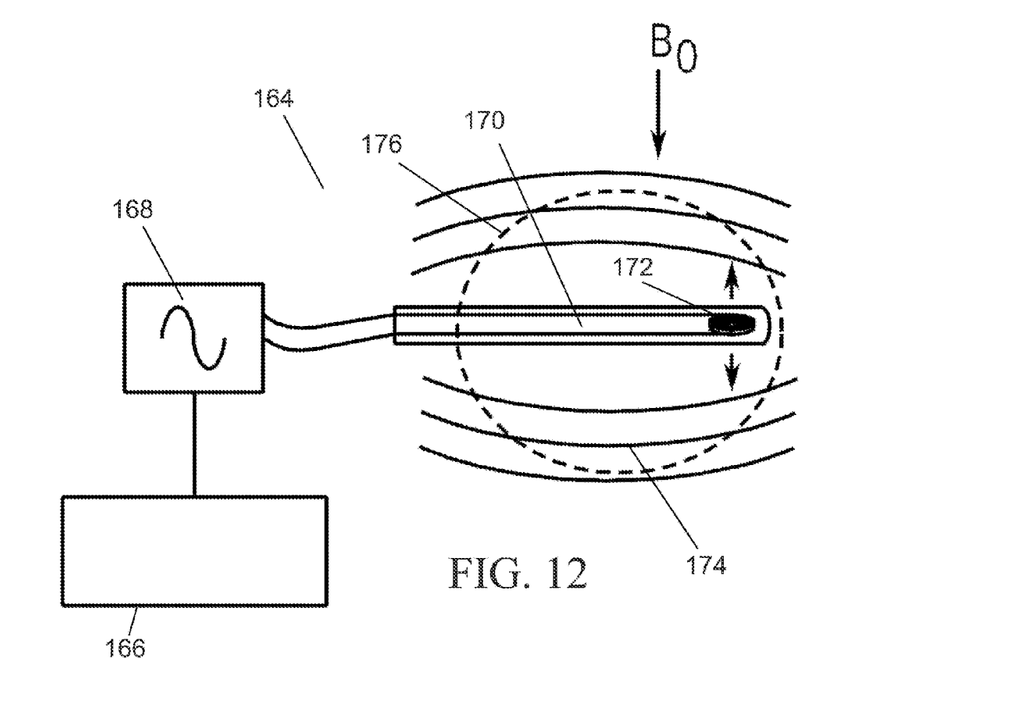
FIG. 12 is a schematic diagram showing an electromagnetic intra-luminal vibratory device according to an embodiment of the invention.

FIG. 12 is a schematic diagram showing an electromagnetic intra-luminal vibratory system 164 according to an embodiment of the invention. System 164 includes a controller 166 coupled to and configured to control a function generator 168. An electromagnetic intra-luminal motion device 170 has a coil 172 therein that is coupled to function generator 168. In the presence of a magnetic field, such as a $B_0$ field generated by an MR system (not shown), application of current in coil 172 causes translation of coil 172 relative to the magnetic field. It is contemplated that function generator 168 may apply either an AC current or a DC current in coil 172. A magnitude and frequency of the current induced in coil 172 affects its vibratory response. Vibration of coil 172 produces shear waves 174 into a tissue region of interest 176.

Figure 13A:
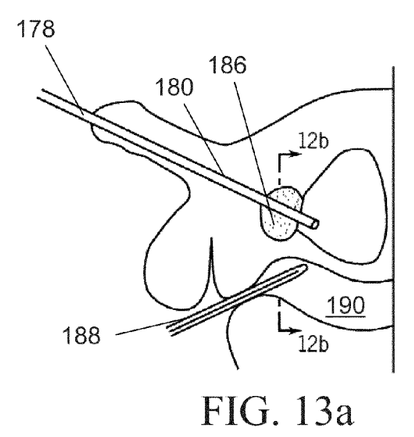
FIGS. 13(a) and 13(b) show schematic diagrams of an intra-luminal vibratory device inserted into a urethra according to an embodiment of the invention.
Figure 13B:
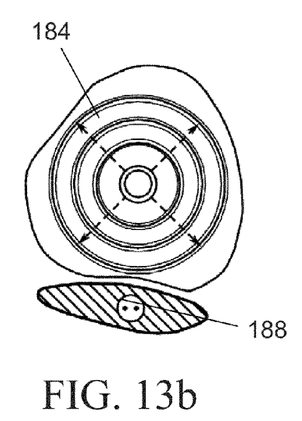

FIGS. 13(a) and 13(b) show schematic diagrams of an intra-luminal vibratory member 178 inserted into a urethra 180 of a patient according to an embodiment of the invention. It is contemplated that device 178 is a member selected from one of the embodiments described herein. Vibration of member, where the vibration is produced by an external acoustic energy source coupled to member 178, causes mechanical waves 184 to propagate through urethra 180 and into a prostate 186. An RF coil 188 is shown inserted into a colon or rectum 190 of the patient such that high-resolution MR data may be locally acquired via RF coil 188. The imaged mechanical waves 184 can be used to calculate the underlying tissue stiffness based on their wavelength. As shown in FIG. 13(b), device 178 creates omnidirectional waves 184 in prostate 186.

Figure 14:
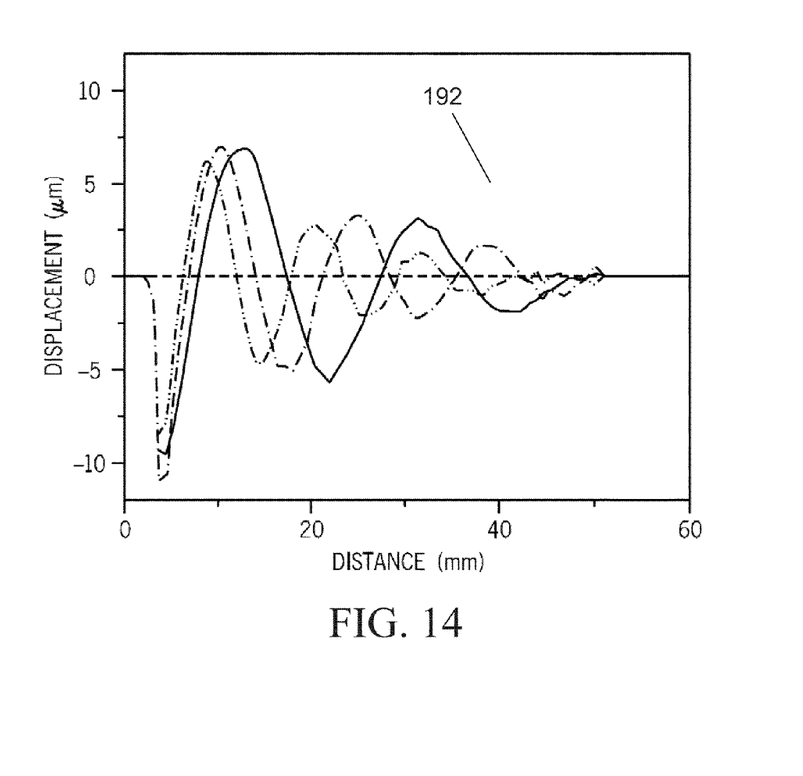
FIG. 14 shows exemplary displacements of motion waves into a gel phantom according to an embodiment of the invention.

FIG. 14 shows exemplary displacements of motion waves into a gel phantom according to an embodiment of the invention. Graph 192 depicts the profile of displacement extending radially from an intra-luminal vibratory member according to an embodiment of the invention. Three frequencies are shown illustrating the influence of attenuation on penetration depth.

Figure 15A:
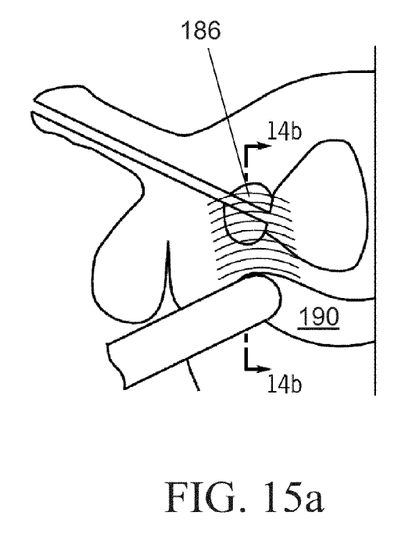
FIGS. 15(a) and 15(b) show schematic diagrams of intra-luminal vibratory devices inserted into a rectum according to an embodiment of the invention.
Figure 15B:
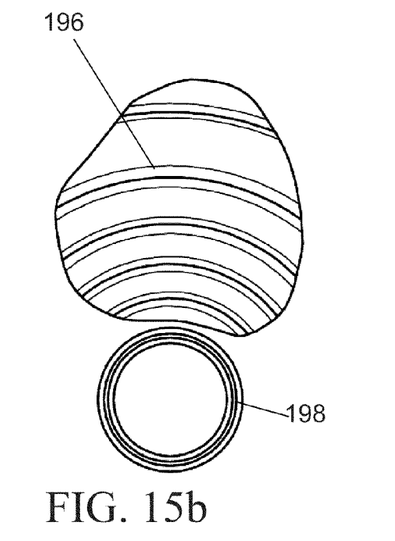

FIGS. 15(a) and 15(b) show schematic diagrams of intraluminal vibratory member 194 inserted into colon 190 of a patient according to an embodiment of the invention. It is contemplated that intra-luminal vibratory member 194 is selected from one of the embodiments described herein. Externally excited vibration of member 194 causes mechanical waves 196 to propagate into prostate 186 and other surrounding tissue. A surface RF coil 198 is shown positioned on patient 182 such that high-resolution MR data may be acquired. As shown in FIG. 15(b), device 194 creates omnidirectional waves 196 in prostate 186.

Figure 16:
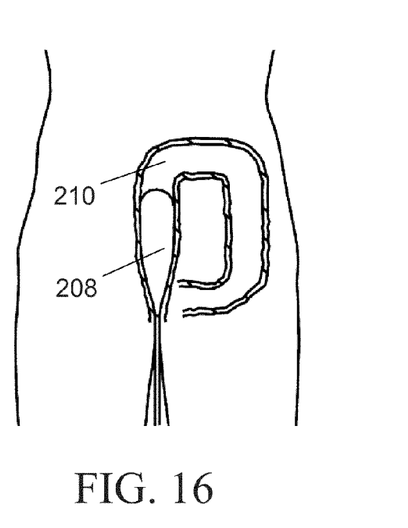
FIG. 16 shows an illustration of an intra-luminal vibratory device inserted into an intestinal cavity according to an embodiment of the invention.
Figure 17:
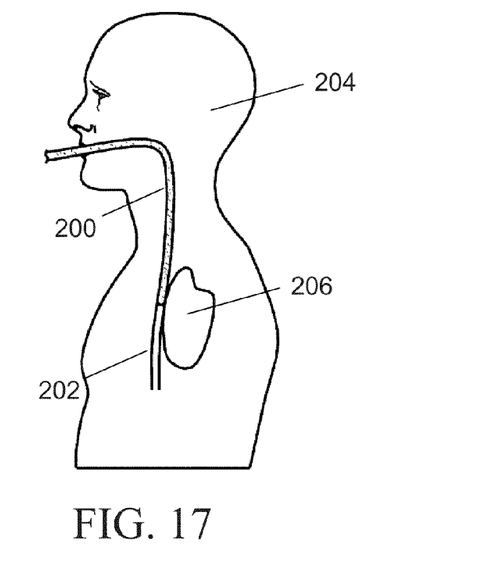
FIG. 17 shows an illustration of an intra-luminal vibratory device inserted into an esophagus according to an embodiment of the invention.

FIGS. 16 and 17 illustrate devices inserted into lumens or cavities according to embodiments of the invention. As shown in FIG. 17, an intra-luminal vibratory member 200 according to aforementioned embodiments of the invention may be inserted into an esophagus 202 of a patient 204 for intracorporeal cardiac elastography of a heart 206 of patient 204. As shown in FIG. 16, member 208 (according to aforementioned embodiments of the invention) may be inserted into a colon or other intestinal portion 210 for intracorporeal elastography of the intestine 210 or other adjacent tissue.

Figure 18:
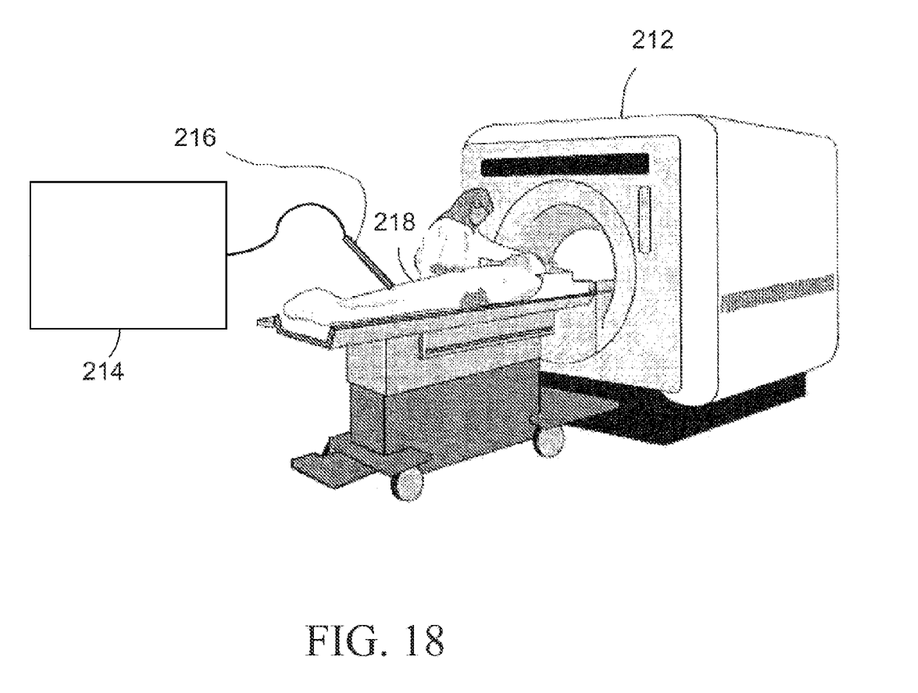
FIG. 18 shows a medical imaging device for use with an intra-luminal vibratory device according to an embodiment of the invention.

FIG. 18 shows a medical imaging system 212 for use with an intra-luminal vibratory member according to an embodiment of the invention. An external energy source 214 is used to produce mechanical or vibratory motion of member 216, which is inserted into a body cavity or orifice (not shown) of a patient 218, via a pneumatic, electromagnetic, piezoelectric, or hydraulic system according to the embodiments described above. The patient 218 and actuator 216 are placed in an MR imager 212 to detect and resolve the propagation of mechanical waves (not shown) in the tissue (not shown) around the actuator 216 for the purposes of stiffness imaging. The energy source 216 can be placed on the actuator itself, or at a distance, depending on the MRI-compatibility of its components. Preferably, the system includes a controller that is configured to control the acoustic energy source synchronously with the imaging sequence of the MRI system.

Embodiments of the invention include an intra-luminal vibratory member configured to fit inside a body cavity or orifice, wherein an acoustic energy source external to the imaging subject is acoustically coupled to the proximal end of the member, and the distal end of the member is adapted to be inserted into a lumen of the subject. In a preferred embodiment, high frequency mechanical shear waves in adjacent tissue may be generated that are desirable for high resolution imaging of tissues in close proximity to the intra-luminal devices. In addition, the capability to bring these actuators closer to the tissue of interest reduces the distance the shear waves need to travel, thus enabling the use of higher frequencies, which are attenuated quickly and can only travel short distances. Higher frequencies can be very important in applications studying thin structures such as the wall of the colon or digestive track, which may only be a few millimeters thick. Structures such as these benefit from frequencies of approximately 1000-3000 Hz in order to resolve their stiffness. Such frequencies may be produced and propagated into tissue regions of interest by an intra-luminal or intra-cavity actuator such as one described in the embodiments above.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

What is claimed is:

1. An apparatus for elastography comprising:
a member, wherein a distal end of said member is adapted to be positioned within a lumen of an imaging subject;
an acoustic energy source provided external to said subject and acoustically coupled to a proximal end of said member; and
wherein acoustic energy coupled to said member generates mechanical motion of said member configured to generate shear waves within said subject.

2. The apparatus according to claim 1 further comprising a magnetic resonance imaging system configured to produce an elastogram.

3. The apparatus according to claim 1 wherein said member is flexible over at least a portion of its length.

4. The apparatus according to claim 1 wherein a frequency of said shear waves falls within a range of 60 Hz and 3000 Hz.

5. The apparatus according to claim 1 wherein said energy source is configured to cause said member to impart one of pulsed mechanical energy and continuous mechanical energy into said subject.

6. The apparatus according to claim 1 wherein said member further comprises a radio-frequency coil, wherein said radio-frequency coil is provided near a distal end of same member, and wherein said radio-frequency coil is addressable from a proximal end of said member.

7. The apparatus according to claim 6 wherein said radio-frequency coil is adapted to enable any one of the generation of a magnetic pulse for the rotation of a magnetic moment within a subject and the detection of a radio-frequency signal to produce an MRI image of a subject.

8. The apparatus according to claim 1 wherein said acoustic energy source produces at least one of longitudinal vibrations of said member and vibratory motion of said member.

9. The apparatus according to claim 8 wherein said acoustic energy source comprises a piezoelectric actuator.

10. The apparatus according to claim 8 wherein a shape of said distal end of said member is adapted to promote contact between said distal end of said member and an inner surface of said lumen.

11. The apparatus according to claim 10 wherein a diameter of said distal end of said member is greater than a diameter of said lumen prior to insertion of said member.

12. The apparatus according to claim 10 wherein said member further comprises an internal volume, wherein said distal end of said member is adapted to expand in diameter in response to a positive pressure change within said internal volume, wherein said member further comprises an external means of varying a pressure within said internal volume, and wherein said external means of varying a pressure may be configured to apply a positive pressure change within said internal volume for the improved adherence of said member to an internal surface of said lumen.

13. The apparatus according to claim 12 wherein said external means of varying a pressure in said internal volume is an inflation device.

14. The apparatus according to claim 10 wherein said member further comprises an internal volume, wherein said distal end of said member comprises one or more openings into said internal volume, wherein said member further comprises an external means of varying a pressure in said internal volume, and wherein said external means of varying a pressure may be configured to apply a negative pressure change within said internal volume for the improved adherence of said member to an internal surface of said lumen.

15. The apparatus according to claim 14 wherein said external means of varying a pressure in said internal volume is a suction device.

16. The apparatus according to claim 1 wherein said member comprises an internal volume containing a fluid, wherein said proximal end of said member is adapted to couple acoustic energy from said acoustic energy source into said fluid, wherein said acoustic energy may propagate within said fluid to a distal end of said member in the form of pressure waves, and wherein a distal end of said member is adapted to generate said shear waves within said subject from said pressure waves.

17. The apparatus according to claim 16 wherein said distal end of said member comprises a membrane in contact with said fluid, wherein pressure waves within said fluid produce vibrations of said membrane and generate shear waves within said subject.

18. The apparatus according to claim 17 wherein said membrane comprises a substantially annular surface.

19. The apparatus according to claim 17 wherein said membrane comprises a substantially planar surface.

20. The apparatus according to claim 17 wherein said member comprises a flexible hose hermetically connected to a distal member, wherein said distal member comprises said membrane, and wherein said hose and said distal member enclose said internal volume containing said fluid.

21. The apparatus according to claim 16 wherein said acoustic energy source comprises an audio system, wherein said acoustic energy source is hermetically coupled to a proximal end of audio system.

22. The apparatus according to claim 21 wherein said audio system comprises a function generator, an audio amplifier, and an audio output device.

23. The apparatus according to claim 16 wherein said acoustic energy source comprises a hydraulic actuator, wherein said hydraulic actuator is hermetically coupled to a proximal end of said member.

24. The apparatus according to claim 23 wherein said hydraulic actuator comprises a piston.

25. The apparatus according to claim 1 wherein said lumen is one of a rectum and a urethra of the imaging subject.

26. A method of intracorporeal elastography, said method comprising the steps of:
positioning a distal end of a member within a lumen of an imaging subject;
coupling acoustic energy from an external acoustic energy source to a proximal end of said member, wherein said acoustic energy coupled to said member generates shear waves within said subject via a mechanical motion of said member; and
acquiring medical imaging data of a region of interest of said subject.

27. The method according to claim 26 wherein said medical imaging data is acquired using a magnetic resonance imaging system configured to produce an elastogram.

28. The method according to claim 26 wherein said member is flexible over at least a portion of its length.

29. The method according to claim 26 wherein a frequency of said shear waves falls within a range of 60 Hz and 3000 Hz.

30. The method according to claim 26 wherein said energy source is configured to cause said member to impart one of pulsed mechanical energy and continuous mechanical energy into said subject.

31. The method according to claim 26 wherein said member further comprises a radio-frequency coil, wherein said radio-frequency coil is provided near a distal end of same member, and wherein said radio-frequency coil is addressable from a proximal end of said member.

32. The method according to claim 26 wherein said acoustic energy source produces at least one of longitudinal vibrations of said member and vibratory motion of said member.

33. The method according to claim 32 wherein a shape of said distal end of said member is adapted to promote contact between said distal end of said member and an inner surface of said lumen.

34. The method according to claim 33 wherein said member further comprises an internal volume, wherein said distal end of said member is adapted to expand in diameter in response to a positive pressure change within said internal volume, wherein said member further comprises an external means of varying a pressure within said internal volume, and wherein said method further comprising applying a positive pressure change within said internal volume for the improved adherence of said member to an internal surface of said lumen.

35. The method according to claim 33 wherein said member further comprises an internal volume, wherein said distal end of said member comprises one or more openings into said internal volume, wherein said member further comprises an external means of varying a pressure in said internal volume, and wherein said method further comprises applying a negative pressure change within said internal volume for the improved adherence of said member to an internal surface of said lumen.

36. The method according to claim 26 wherein said member comprises an internal volume containing a fluid, wherein said proximal end of said member is adapted to couple acoustic energy from said acoustic energy source into said fluid, wherein said acoustic energy propagates within said fluid to a distal end of said member in the form of pressure waves, and wherein a distal end of said member is adapted to generate said shear waves within said subject from said pressure waves.

37. The method according to claim 36 wherein said distal end of said member comprises a membrane in contact with said fluid, wherein pressure waves within said fluid produce vibrations of said membrane and generate shear waves within said subject.

38. The method according to claim 26 wherein said member is inserted into one of a rectum and a urethra of said imaging subject.

39. The method according to claim 26 further comprising inserting a radiofrequency coil into a cavity adjacent to the region of interest.

40. A system for elastography comprising:
a member, wherein a distal end of said member is adapted to be positioned within a lumen of an imaging subject;
an acoustic energy source provided external to said subject and acoustically coupled to a proximal end of said member, wherein acoustic energy coupled to said member generates mechanical movement of said member, and wherein said mechanical movement generates shear waves within said subject; and
a medical imaging apparatus configured to detect a response of tissue to said shear waves.

41. The system according to claim 40 wherein said medical imaging apparatus comprises a magnetic resonance imaging system configured to produce an elastogram.

42. The system according to claim 40 wherein said member is flexible over at least a portion of its length.

43. The system according to claim 40 wherein a frequency of said shear waves falls within a range of 60 Hz and 3000 Hz.

44. The system according to claim 40 wherein said energy source is configured to cause said member to impart one of pulsed mechanical energy and continuous mechanical energy into said subject.

45. The system according to claim 40 wherein said member further comprises a radio-frequency coil, wherein said radio-frequency coil is provided near a distal end of same member, and wherein said radio-frequency coil is addressable from a proximal end of said member.

46. The system according to claim 40 wherein said acoustic energy source produces at least one of longitudinal vibrations of said member and vibratory motion of said member.

47. The system according to claim 46 wherein said acoustic energy source comprises a piezoelectric actuator.

48. The system according to claim 46 wherein a shape of said distal end of said member is adapted to promote contact between said distal end of said member and an inner surface of said lumen.

49. The system according to claim 48 wherein said member further comprises an internal volume, wherein said distal end of said member is adapted to expand in diameter in response to a positive pressure change within said internal volume, wherein said member further comprises an external means of varying a pressure within said internal volume, and wherein said external means of varying a pressure may be configured to apply a positive pressure change within said internal volume for the improved adherence of said member to an internal surface of said lumen.

50. The system according to claim 48 wherein said member further comprises an internal volume, wherein said distal end of said member comprises one or more openings into said internal volume, wherein said member further comprises an external means of varying a pressure in said internal volume, and wherein said external means of varying a pressure may be configured to apply a negative pressure change within said internal volume for the improved adherence of said member to an internal surface of said lumen.

51. The system according to claim 40 wherein said member comprises an internal volume containing a fluid, wherein said proximal end of said member is adapted to couple acoustic energy from said acoustic energy source into said fluid, wherein said acoustic energy may propagate within said fluid to a distal end of said member in the form of pressure waves, and wherein a distal end of said member is adapted to generate said shear waves within said subject from said pressure waves.

52. The system according to claim 51 wherein said distal end of said member comprises a membrane in contact with said fluid, wherein pressure waves within said fluid produce vibrations of said membrane and generate shear waves within said subject.

53. The system according to claim 52 wherein said member comprises a flexible hose hermetically connected to a distal member, wherein said distal member comprises said membrane, and wherein said hose and said distal member enclose said internal volume containing said fluid.

54. The system according to claim 51 wherein said acoustic energy source comprises an audio system, wherein said acoustic energy source is hermetically coupled to a proximal end of audio system.

55. The system according to claim 51 wherein said acoustic energy source comprises a hydraulic actuator, wherein said hydraulic actuator is hermetically coupled to a proximal end of said member.

56. The system according to claim 40 further comprising a radiofrequency coil adapted to be inserted into a cavity adjacent to a region of interest.

57. The system of claim 40 further comprising a controller configured to control said acoustic energy source synchronously with an imaging sequence of said medical imaging apparatus.

58. An apparatus for elastography comprising:
a member, wherein a distal end of said member is adapted to be positioned within a lumen of an imaging subject;
an acoustic energy source provided external to said subject and acoustically coupled to a proximal end of said member;
wherein acoustic energy coupled to said member generates shear waves within said subject; and
wherein said energy source is configured to cause said member to impart one of pulsed mechanical energy and continuous mechanical energy into said subject.

* * * * *